(12) United States Patent
Handa et al.

(10) Patent No.: US 8,045,141 B2
(45) Date of Patent: Oct. 25, 2011

(54) DETECTING ELEMENT, DETECTING DEVICE AND DETECTING METHOD

(75) Inventors: Yoichiro Handa, Tokyo (JP); Satoru Nishiuma, Kawasaki (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 12/296,426

(22) PCT Filed: May 8, 2007

(86) PCT No.: PCT/JP2007/059818
§ 371 (c)(1),
(2), (4) Date: Oct. 7, 2008

(87) PCT Pub. No.: WO2007/132795
PCT Pub. Date: Nov. 22, 2007

(65) Prior Publication Data
US 2009/0109422 A1    Apr. 30, 2009

(30) Foreign Application Priority Data
May 12, 2006    (JP) .................................. 2006-133847

(51) Int. Cl.
G01N 33/48    (2006.01)
G01N 21/55    (2006.01)
(52) U.S. Cl. .......................................... 356/39; 356/445
(58) Field of Classification Search .............. 356/36–42, 356/445–448; 435/6, 7.2; 436/164, 171, 436/172; 422/82.08; 250/288, 281, 282
See application file for complete search history.

(56) References Cited

U.S. PATENT DOCUMENTS

| | | | | |
|---|---|---|---|---|
| 5,281,935 A | * | 1/1994 | Knecht et al. | 333/187 |
| 5,321,276 A | * | 6/1994 | Kurakado et al. | 257/32 |
| 6,331,276 B1 | * | 12/2001 | Takei et al. | 422/82.09 |
| 6,441,945 B1 | | 8/2002 | Atwater et al. | |
| 6,778,316 B2 | * | 8/2004 | Halas et al. | 359/296 |
| 7,079,250 B2 | * | 7/2006 | Mukai | 356/445 |
| 7,088,449 B1 | * | 8/2006 | Brongersma | 356/445 |
| 7,294,826 B2 | * | 11/2007 | Tomaru | 250/236 |

(Continued)

FOREIGN PATENT DOCUMENTS

JP    3504076    9/1991

(Continued)

OTHER PUBLICATIONS

PCT International Search Report and Written Opinion of the International Searching Authority, Mailing Date Aug. 14, 2007.

(Continued)

*Primary Examiner* — Sang Nguyen
(74) *Attorney, Agent, or Firm* — Fitzpatrick, Cella, Harper & Scinto

(57) ABSTRACT

The present invention provides a detecting element which can stably detect a substance with high sensitivity; a detecting device therefor; and a detecting method therefor. The detecting element and the detecting device according to the present invention have a plurality of planes having a plurality of mutually-separated metallic structures arranged thereon. The detecting method according to the present invention includes making a detecting light irradiate the detecting element so that the light can intersect a plurality of the planes. Thereby, the detecting light is more frequently absorbed in the vicinity of the metallic structure and the detecting device can stably detect a slight change of a spectrum originating from a trace change of a refractive index occurring in the vicinity of the metallic structure, with the high sensitivity.

11 Claims, 8 Drawing Sheets

U.S. PATENT DOCUMENTS

| | | |
|---|---|---|
| 7,351,588 B2 * | 4/2008 | Poponin .................. 436/171 |
| 7,387,901 B2 | 6/2008 | Nishiuma et al. |
| 7,387,967 B2 * | 6/2008 | Ogawa et al. ............. 438/706 |
| 7,403,287 B2 * | 7/2008 | Ogawa et al. ............. 356/445 |
| 7,403,683 B2 * | 7/2008 | Chern et al. ............... 385/39 |
| 7,425,310 B2 * | 9/2008 | Truex et al. ............. 422/82.05 |
| 7,456,383 B2 * | 11/2008 | Kim et al. ................. 250/226 |
| 7,476,787 B2 * | 1/2009 | Thomas et al. ........... 250/306 |
| 7,583,379 B2 * | 9/2009 | Zhao et al. ............... 356/301 |
| 7,643,156 B2 * | 1/2010 | Naya et al. ............... 356/519 |
| 7,705,989 B2 * | 4/2010 | Chaton et al. ............ 356/445 |
| RE41,762 E * | 9/2010 | Lopez et al. .............. 210/632 |
| 2002/0115224 A1 | 8/2002 | Rudel et al. |
| 2002/0186469 A1 * | 12/2002 | Kawazu et al. ............. 359/486 |
| 2004/0185448 A1 * | 9/2004 | Lopez-Avila et al. ........... 435/6 |
| 2005/0136483 A1 * | 6/2005 | Carlson ....................... 435/7.1 |
| 2006/0170918 A1 | 8/2006 | Nishiuma |
| 2007/0285666 A1 | 12/2007 | Utsunomiya et al. |
| 2008/0273207 A1 | 11/2008 | Sekiguchi et al. |
| 2008/0316486 A1 | 12/2008 | Nishiuma et al. |

FOREIGN PATENT DOCUMENTS

| | | |
|---|---|---|
| JP | 10-267841 | 10/1998 |
| JP | 11-326193 | 11/1999 |
| JP | 2000-356587 | 12/2000 |
| JP | 2003-315258 | 11/2003 |
| JP | 2004531703 | 10/2004 |
| JP | 2005-181296 | 7/2005 |
| JP | 2005-283556 | 10/2005 |
| JP | 2006-10534 | 1/2006 |
| JP | 2006-84359 | 6/2006 |
| WO | 89-10788 | 11/1989 |
| WO | 01-13149 | 2/2001 |
| WO | 02-066162 | 8/2002 |
| WO | 2005-085806 | 9/2005 |

OTHER PUBLICATIONS

U.S. Appl. No. 12/279,985, filed Mar. 20, 2007, Isaka, et al.
U.S. Appl. No. 12/159,391, filed Jan. 17, 2007, Nishiuma, et al.
U.S. Appl. No. 12/088,023, filed Dec. 20, 2006, Yamamichi, et al.
PCT International Preliminary Report on Patentability, Mailing Date Nov. 28, 2008.

* cited by examiner

DETECTING ELEMENT, DETECTING DEVICE AND DETECTING METHOD

TECHNICAL FIELD

The present invention relates to a detecting element for detecting characteristics of an analyte, a detecting device therefor, and a detecting method therefor.

BACKGROUND ART

In recent years, with the increasing awareness of health issues, environmental issues and issues of safety on food, methods for detecting substances related to these issues (so-called chemical substances like substance related to living body (hereafter referred to as a target substance)) have been demanded.

A detecting technique with high sensitivity is often required for detecting a target substance. This is because a collectable amount of a sample containing the target substance is often very small, and furthermore, even the sample occasionally contains only a trace amount of the target substance among variously mixed substances, as in the case of protein in blood. For this reason, a technique for detecting the target substance has been demanded which has such a high sensitivity as to be capable of detecting a trace amount of the target substance contained in a trace amount of an analyte.

One technique for responding such a demand is a measurement method with the use of a plasmon resonance phenomenon occurring around a metallic particle, which is being developed.

Japanese Patent No. 3,452,837 discloses a technique of detecting how much substance has been absorbed by or has deposited on a fine metallic particle fixed on a substrate, by using a plasmon resonance phenomenon occurring around the fine metallic particle, measuring the change of an absorption spectrum of a light having passed through a medium, and detecting the change of a refractive index of the medium.

In addition, Japanese Patent Application Laid-Open No. 2005-283556 discloses a technique of measuring a change of an absorption spectrum for a transmitted light at high sensitivity, by projecting measuring light into a narrow duct having a plurality of fine metallic particles arranged therein.

In the technique according to Japanese Patent No. 3,452,837, it is assumed that a substrate having a lower density of fine metallic particles would more easily detect a change of an absorption spectrum, because the measured absorption spectrum shows only the absorption spectrum of a single fine metallic particle and is hardly affected by interaction between the fine metallic particles. However, it is also assumed that when the substrate has a lower density of fine metallic particles thereon, an absolute absorbance of a spectrum decreases, because the number of fine metallic particles per unit area becomes few. When the absorbance of the spectrum decreases, it becomes difficult to measure characteristics of the absorption spectrum, and consequently to stably detect the change of the spectrum at high sensitivity with a detector, which is a problem.

On the other hand, the technique in Japanese Patent Application Laid-Open No. 2005-283556 can increase the absorbance of the spectrum. However, the technique has a problem that it is difficult to produce such an element that gives rise to less interaction between metallic nanoparticles.

DISCLOSURE OF THE INVENTION

An object of the present invention is to provide a detecting element which can stably detect a target substance at high sensitivity; a detecting device therefor; and a detecting method therefor.

The present invention is directed to a detecting element for detecting a property of an analyte by using a detecting light, comprising a plurality of metallic structures separated from each other, a substrate having a plane on which the metallic structures exist, and an analyte-holding region at least one part of which is comprised of a part of the plane, a plurality of the planes existing in the detecting element, and one of the planes having a normal line intersecting with all the other planes.

The plane having the normal line can be one arbitrarily selected from the planes.

The metallic structure can have a surface by which a capturing body for capturing a target substance contained in the analyte is held.

The metallic structures can be patterned and have their respective flat shapes.

The present invention is directed to a detecting device for detecting a property of an analyte, comprising a detecting element, a light source for irradiating the detecting element with a detecting light, a light receiving element for receiving an output light emitted from the detecting element, and an arithmetic unit for processing a signal obtained by the light receiving element to determine the property of the analyte, wherein the detecting element comprises a plurality of metallic structures separated from each other, a substrate having a plane on which the metallic structures exist, and an analyte-holding region at least one part of which is comprised of a part of the plane, a plurality of the planes existing in the detecting element, and one of the planes having a normal line intersecting with all the other planes.

The plane having the normal line can be one arbitrarily selected from the planes.

In the detecting device, a plurality of the planes can exist in a traveling path of the detecting light, and, the normal line intersecting with the other planes can be on an angle of 20 degrees or less with the detecting light.

The present invention is directed to a method for detecting a property of an analyte using a detecting element which is comprised of a plurality of metallic structures separated from each other, a substrate having a plane on which the metallic structures exist, and an analyte-holding region at least one part of which is comprised of a part of the plane, and has a plurality of the planes, which comprises the steps of:

introducing an analyte into the analyte-holding region;

irradiating the detecting element with a detecting light so that the detecting light intersects a plurality of the planes;

receiving the output light emitted from the detecting element with a light receiving element; and determining a property of the analyte by a signal output from the light receiving element.

In the irradiating step the detecting element can be irradiated with the detecting light so that a plurality of the planes exist in a traveling path of the detecting light, and, each normal line of the planes is on an angle of 20 degrees or less with the detecting light.

The present invention is directed to a detecting element for detecting characteristics of a liquid analyte by using a detecting light, characterized in that the detecting element has an analyte-holding region and a substrate having a plurality of planes having a plurality of mutually-separated metallic structures arranged thereon, wherein the plane functions as a wall surface of the analyte-holding region, and the detecting element has a plurality of the planes so as to make the plane intersect the detecting light.

The present invention is directed to a device for detecting characteristics of a liquid analyte, characterized in that the device has a detecting element, a light source for emitting a detecting light toward the detecting element, a light receiving element for receiving the light having passed through the detecting element, and an arithmetic unit for determining the characteristics of an analyte based on a signal obtained from the light receiving element, wherein the detecting element has a analyte-holding region and a substrate having a plurality of planes each of which functions as a wall surface of the analyte-holding region, and has a plurality of mutually-separated metallic structures arranged thereon so as to make the plane intersect the detecting light.

The present invention is directed to a method for detecting characteristics of a liquid analyte, characterized by the steps of: introducing the liquid analyte into a analyte-holding region of a detecting element that has the liquid-analyte-holding region and a substrate having a plurality of planes having a plurality of mutually-separated metallic structures arranged thereon, each of which functions as a wall surface of the analyte-holding region; making a detecting light irradiate the detecting element so that the light can intersect a plurality of the planes; making a light receiving element receive the light which has passed through the detecting element; and determining characteristics of the liquid analyte based on a signal output from the light receiving element.

The order of the above steps is not specified in the above method for detecting the characteristics of the analyte or liquid analyte.

In the above described present invention, the surface of the metallic structure can have a capturing body for selectively or specifically capturing a target substance contained in an analyte. In addition, the above described metallic structure can be a patterned flat structure.

Further features of the present invention will become apparent from the following description of exemplary embodiments with reference to the attached drawings.

BEST MODES FOR CARRYING OUT THE INVENTION

In the next place, embodiments for carrying out the present invention will be described. However, the present invention is specified by claims, and is not limitedly interpreted into the following aspects and embodiments. The present invention can be realized by freely changing, for instance, a material of the following aspects and embodiments, a composition condition, a reaction condition and the arrangement of a member or an element, in a range understandable by those skilled in the art.

At first, a detecting element according to the present invention will be now described.

A detecting element according to the present invention is an element for detecting characteristics of an analyte with the use of a detecting light. The sentence of detecting characteristics of an analyte means detecting any characteristic including physical characteristics and chemical characteristics of the analyte. An easily-understandable example of detecting the characteristics of the analyte includes the case of detecting the chemical characteristics (such as presence or absence of an interaction between the analyte and a component in the detecting element), by using the physical characteristics (such as optical characteristics) of the element. A more specific example of a method for measuring the presence or absence of, or the concentration of the target substance in the analyte includes the steps of: making the analyte contact with the element; making a detecting light irradiate the element; making a light receiving element detect light emitted from the element, and measuring the change of the characteristics between the detecting light and the emitted light. The above analyte which is an object to be detected by a detecting element according to the present invention may be not only in a liquid state but also in a state other than the liquid state, such as a gaseous state. However, from the viewpoint of detection easiness, the analyte can be in a liquid state.

Figure 1A:
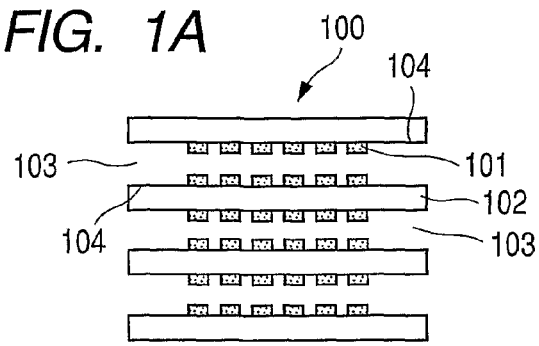
FIGS. 1A, 1B, 1C, 1D, 1E, 1F and 1G are schematic sectional views illustrating some examples of a substrate having a plane that has a plurality of mutually-separated metallic structures thereon, which is suitably used in the present invention.
Figure 1B:
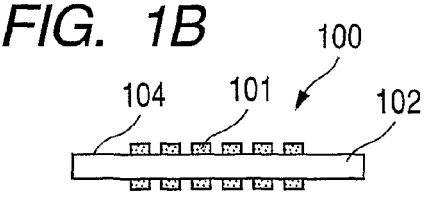

FIG. 1A illustrates an example of a detecting element according to the present invention.

A detecting element 100 has a plurality of metallic structures 101, a substrate 102 and an analyte-holding region 103, and a plurality of the metallic structures 101 arranged on a plane 104 of the substrate 102 so as to be separated from each other. Specifically, the substrate 102 has the plane 104 having a plurality of the metallic structures 101 arranged thereon so as to be separated from each other. In addition, any one plane among a plurality of the planes 104 having the metallic structure arranged thereon has a normal line which intersects with all the other planes. Incidentally, "the plane having a plurality of mutually-separated metallic structures arranged thereon" may be hereafter referred to merely as "a plane having a metallic structure arranged thereon". In addition, at least one of the analyte-holding region 103 has one part of the plane having a plurality of the metallic structures 101 arranged thereon.

Figure 2:
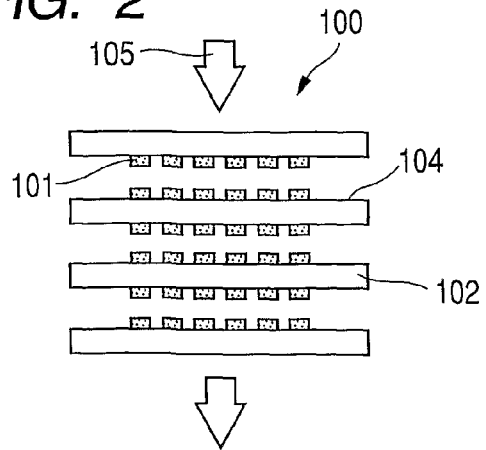
FIG. 2 is a schematic block diagram illustrating an example of the relation between a detecting light and a detecting element.

Specifically, a plurality of planes 104 having a metallic structure arranged thereon are configured so as to intersect a light (detecting light) 105 incident on a detecting element 100, for instance, as is illustrated in FIG. 2. In the present invention, "the planes are configured so as to intersect detecting light" means that the above described plane and the above described detecting light exist in a non-parallel state (further preferably in a perpendicular state or an appropriately perpendicular state), and the above described plane exists in a path of the above described detecting light. Here, the approximately perpendicular state means an intersecting angle of 90 degrees±20 degrees. Accordingly, an angle formed by a normal line of the plane 104 having the above described metallic structure 101 arranged thereon and the above described detecting light 105 can be within 20 degrees.

In the above description, when a detecting light has a three-dimensional form such as a cylindrical column and a rectangular solid instead of a linear form, a straight line existing in a center of the three-dimensional form is considered as a base when determining an angle.

Figure 1E:
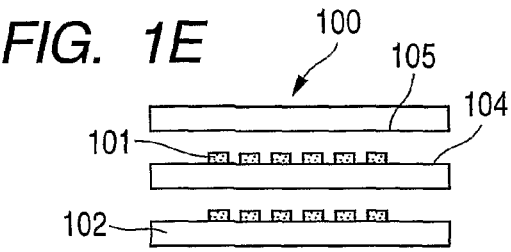
Figure 1C:
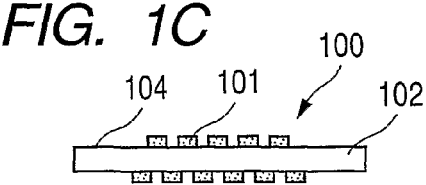
Figure 1F:
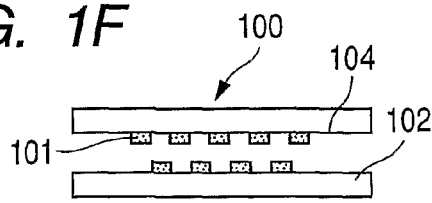
Figure 1D:
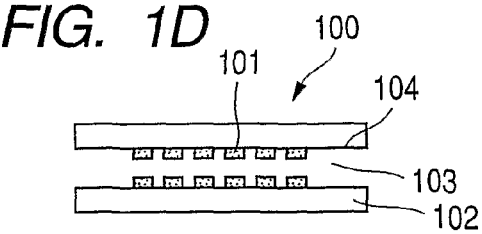

A configuration of an element having a plurality of planes having a metallic structure arranged thereon prepared so as to intersect a detecting light is not limited to the configuration of the element in which the metallic structure 101 exists in each of the facing planes of substrates that are arranged so as to face to each other, and in which an analyte-holding region 103 is sandwiched by planes 104 having the metallic structure arranged thereon, as is illustrated in FIGS. 1A and 1D. The element may have a configuration, for instance, as is illustrated in FIG. 1E, in which there are a plurality of the substrates 102 having the plane 104 having the metallic structure arranged thereon, and there are the plane 104 having the metallic structure arranged thereon and a plane 105 having no metallic structure arranged thereon alternately. Such an element is also conceivable as to have a substrate including the plane 104 having the metallic structure arranged on its both surfaces (like elements illustrated in FIGS. 1B and 1C). A metallic structure existing on an arbitrary plane and a metallic structure existing on a different plane from the above described plane, out of a plurality of planes having a metallic structure arranged thereon, may be symmetric with respect to a plane parallel to the plane having the metallic structure formed thereon, or may not be symmetric. Specifically, the symmetric case with respect to the plane parallel to a plane having the metallic structure formed thereon is illustrated in FIGS. 1A, 1B, 1D and 1E, and the asymmetric case is illustrated in FIGS. 1C and 1F.

Figure 1G:
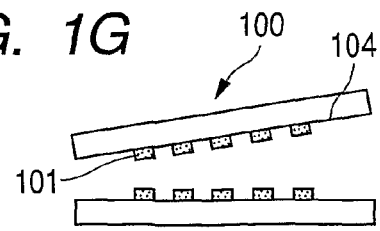

In addition, as for a plurality of planes having a metallic structure arranged thereon, an arbitrary plane out of a plurality of the above described planes can possess such a normal line as to intersect with all the other planes, but any one plane has only to possess such a normal line as to intersect with all the other planes. Accordingly, for instance, as is illustrated in FIG. 1G, the planes 104 having the metallic structure arranged thereon may not be parallel to each other.

Figure 3:
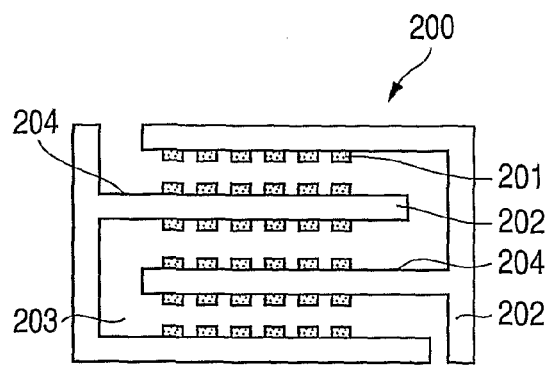
FIG. 3 is a schematic sectional view illustrating an example in which a plurality of substrates having a plane that has a metallic structure arranged thereon is combined to form a duct for an analyte.

It goes without saying that there are variously modified examples in a range of the present invention in addition to the above examples. For instance, as is illustrated in FIG. 3, a duct for a analyte may be formed by combining a plurality of substrates 202 having a plane having a metallic structure 201 arranged thereon with another one.

In any example, when a detecting element according to the present invention is used for measurement, a detecting light incident on the element passes through a plurality of planes having a metallic structure arranged thereon, and is emitted from the element. Thus configured element can stably detect a slight change in a spectrum at high sensitivity which has been caused by a slight change of a refractive index in the vicinity of the metallic structure, because the above described detecting light is more frequently absorbed by the metallic structure.

One of a remarkable effect in the present invention obtained by arranging a metallic structure on a plane of a substrate is that the detecting element can be more easily produced. More specifically, because the substrate is planar, it is facilitated to form a pattern on the substrate, in which metallic structures are separated from each other, or to pretreat the substrate before fixing the metallic structure on the substrate.

In addition, a detecting element according to the present invention can have a capturing body for selectively capturing a target substance in a analyte on the surface of itself (further preferably on the surface of a metallic structure). The element thus having the capturing body thereon can detect the presence or absence of, or the concentration of the target substance in the analyte.

In the next place, each part composing a detecting element 100 illustrated in FIGS. 1A to 1G will be described in detail.

(Substrate)

A substrate 102 may be any material as long as it has a plane 104 for arranging a plurality of metallic structures 101 thereon. Among those, the material can have high transmissivity for a detecting light in particular, because the material had better not obstruct the transmission of the detecting light. The material having the high transmissivity for the detecting light includes, for instance, silica, quartz, PMMA (polymethyl methacrylate) and polystyrene. In addition, the substrate 102 may have a layered structure consisting of a plurality of layers, or may be formed by layering the above described materials. In addition, as for a shape of the substrate, the substrate can have generally a polyhedral shape such as a rectangular solid shape, and more generally can have a tabular shape (which is also one of rectangular solid). The shape of the substrate is not limited to those, but the substrate may have a shape formed by combining substrates 202 with each other, which have the metallic structure 201 arranged thereon, have a comb shape, and have a plane 204 having the metallic structure arranged thereon, as is illustrated in FIG. 3. (Plane having metallic structure arranged thereon)

A plane 104 having a plurality of metallic structures arranged thereon is one part of the surface of a substrate 102.

Planes 104 having a plurality of metallic structures arranged thereon can be defined as two surfaces with the maximum area among the planes belonging to a tabular substrate 102, as is illustrated in FIGS. 1A to 1D, for instance. (Hereafter, when areas of two facing planes among the planes of the substrate are larger than those of the other planes, each of the two facing planes shall be referred to as "main plane"). Here, "plane" in the present invention shall mean a flat face (which is not a curved surface) with a surface roughness of 5 nm or less. A substrate 102 has generally a polyhedron shape such as a rectangular solid shape, as described above, so that one surface of the polyhedron can be used as the plane having the metallic structure arranged thereon. More generally, the substrate 102 has a tabular shape, so that one surface of the tabular substrate can be used as the plane.

However, the plane having the metallic structure arranged thereon does not need to be one surface of a polyhedron. At least one region in a substrate through which a detecting light passes has only to include the plane having the metallic structure arranged thereon. As a matter of course, all the surfaces of the substrate do not necessarily need to be a planar shape.

In addition, the substrate having the plane having the metallic structure arranged thereon is not necessarily a boundary region between an analyte and the outside. In other words, both sides of the substrate (both of the regions separated by the substrate) are an analyte-holding region. In this case, the analyte shall exist on both sides of the substrate when it is measured.

When opposed planes 104 having the metallic structure arranged thereon exist, an analyte-holding region is composed by being sandwiched by the planes 104, and an analyte is passed through the analyte-holding region when being measured, as is illustrated in FIG. 1D, a space between the above described planes can be in a range from 300 nm to 1 mm. This is because when the space between the planes 104 having the metallic structure arranged thereon is too narrow, plasmons existing in metallic structures interact with each other and affect a distribution/intensity of a spatial electric field, whereby the sensitivity of a sensor may decrease. This is also because when the space is too wide, the reaction efficiency of a target substance in the analyte with a capturing body on the surface of the metallic structure may decrease. In view of the flowability of analyte without such a decrease of the reaction efficiency, the distance in the range from 20 μm to 200 μm between the planes is preferable.

(Analyte-Holding Region)

An analyte-holding region 103 has a role of holding an analyte, and has a role as a field for making the analyte contact with a capturing body of a detecting element, when the detecting element has the capturing body. Analyte-holding region 103 means a gap at least one part of which is formed by a part of plane 104 of a substrate 102 on which plane metallic structures 101 are arranged. In more detail, at least one part of analyte-holding region 103 is formed by at least one part of the plane which part has no metallic structure 101 (hereinafter also referred to as "the part without metallic structure") and a surface of metallic structure 101, which surface is not in contact with plane 104 (hereinafter also referred to as "free surface of metallic structure"). More specifically, in examples illustrated in FIGS. 1A, 1D and 1F, analyte-holding region 103 means a gap between regions on substrates 102, each of which regions consists of a part without metallic structure of plane 104 of substrate 102 and the free surface of metallic structure 101. In the example illustrated in FIG. 1E, analyte-holding region 103 means a gap between a region consisting of the part without metallic structure of plane 104 of substrate 102 and the free surfaces of metallic structures 101 and a plane 105 of another substrate which has no metallic structure. In examples illustrated in FIGS. 1B and 1C, analyte-holding region 103 means a gap between a region consisting of the part without metallic structure of plane 104 of substrate 102 and the free surfaces of metallic structures 101 and a member other than the substrate such as a wall surface of a duct in which the detecting element 100 exists.

As described above, an analyte-holding region 103 is a gap, so that a sentence "(A) composes at least one part of an analyte-holding region 103" means that (A) (when (A) has thickness, surface of (A)) exists in a boundary between the analyte-holding region 103 and a part except the analyte-holding region, and is not included in the analyte-holding region.

In addition, when a layer such as an adhesive layer exists between a substrate and a metallic structure, the substrate is considered to have a layered structure, and the surface of the layer is considered to compose at least one part of a plane having the metallic structure arranged thereon. In other words, a part having the metallic structure arranged thereon, in the above described layer provided on the substrate, is defined as a part having the metallic structure arranged thereon, in the plane of the substrate, which has the metallic structure arranged thereon. In addition, a part having no metallic structure arranged thereon, in the above described layer provided on the substrate, is defined as a part having no metallic structure arranged thereon, in the plane of the substrate, which has the metallic structure arranged thereon.

A detecting element can be composed by: using a plurality of substrates; and connecting planes perpendicular to the plane having the above described metallic structure thereon, with each other through an adhesive or the like, or fixing the above described plane to a wall surface of a duct for an analyte. In such a case, at least one part of an analyte-holding region has: at least one part of a region having no metallic structure thereon, in a plane having the metallic structure arranged thereon; a surface of the metallic structure, which does not contact with the above described plane; and an adhesive layer.

An analyte-holding region 103 may have such a structure as to hold an analyte in an immovable state (structure of so-called batch system), but can have such a structure as to hold the analyte in a movable state. In other words, the analyte-holding region 103 can be one part of a duct through which the analyte passes. In this case, it is acceptable to irradiate the analyte with a detecting light while circulating the analyte in the analyte-holding region, or to irradiate the analyte with the detecting light after intercepting the circulation of the analyte.

Figure 4A:
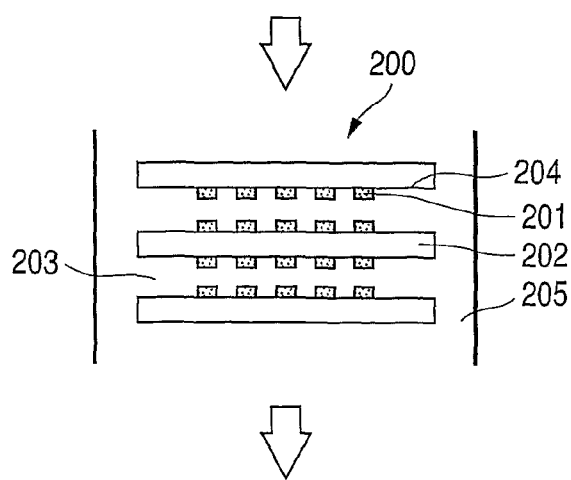
FIGS. 4A and 4B are schematic block diagrams illustrating an example of the relation between the detecting element and the duct of the analyte.
Figure 4B:
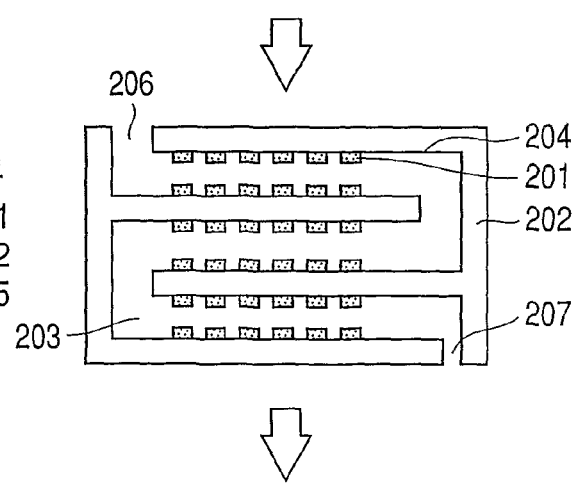

When an analyte-holding region is one part of a duct, it is acceptable to place a detecting element 200 in itself in the duct 205 as is illustrated in FIG. 4A, or to form at least one part of the duct with the analyte-holding region 203 in itself, which is one part of the detecting element 200, as is illustrated in FIG. 4B. In the Figures, an inlet 206 and an outlet 207 are found.

When the duct is formed by the analyte-holding region 203 as is described above, the analyte can be easily introduced into the detecting element 200, and the detecting element 200 can be easily cleaned as needed. For instance, in the case of FIG. 4B, the analyte can be introduced and the detecting element 200 can be cleaned, both by using the inlet 206 and the outlet 207. A capturing body may be immobilized on the detecting element before the detecting element is set in a detecting device according to the present invention, or may be immobilized after the detecting element has been set.

(Metallic Structure)

A metallic structure according to the present invention may be any structure, as long as structures are separately arranged from each other on the above described plane.

A metal which composes a metallic structure can be a metal which gives rise to a plasmon resonance phenomenon, because a measuring method according to the present invention employs a localized surface plasmon resonance technique. Specifically, the metal includes gold, silver, copper, aluminum, platinum, and zinc; an alloy formed of two or more of these elements; and an alloy containing at least one of these elements. More preferably, the metal is gold or silver, which remarkably gives rise to a localized surface plasmon resonance.

A shape of a metallic structure includes a shape which is not polyhedral, such as a spherical shape and an approximately spherical shape; a shape formed by cutting out one part from the spherical shape or the approximately spherical shape; a cylindrical column; a polygonal column; a circular cone; a pyramid; a ring shape with thickness; and various polyhedral shapes such as a cube type shape and an two-by-two matrix shape. A metallic particle can be used as the metallic structure. The metallic particle does not need to be a sphere but may be a polyhedron or the like.

Figure 6A:
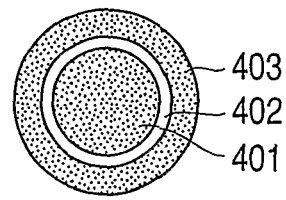
FIGS. 6A, 6B, 6C, 6D, 6E, 6F, 6G, 6H, 6I and 6J are schematic block diagrams illustrating some examples of a shape of a metallic structure used in the present invention.

When a metallic particle is used as a metallic structure, a core shell type metallic particle having a metallic colloid or a dielectric substance as a nucleus may be used. An example of the core shell type metallic particle includes a particle having a cross section which shows a shell structure consisting of a metallic core (metallic colloid) 401, a dielectric shell layer 402 and a metallic shell layer 403, as is illustrated in FIG. 6A. However, the number of the layer, a material and a layered order of the shell layer, and a shape of the metallic particle are not limited to the above example.

When a metallic structure is a fine metallic particle, the metallic structure has a size which can be generally referred to as that of the fine metallic particle, and can have a diameter of 10 nm or larger but 500 nm or smaller. When the metallic particle is not a sphere, the particle diameter is considered to be a diameter obtained by a commercially-available instrument for measuring a particle diameter.

Figure 5A:
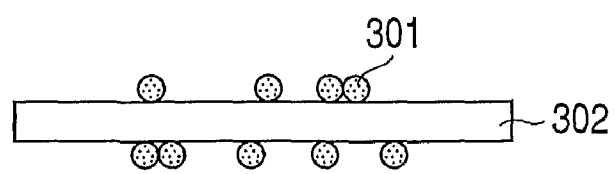
FIGS. 5A, 5B and 5C are schematic sectional views illustrating some examples of a substrate having a plane that has a plurality of mutually-separated metallic structures arranged thereon, which is suitably used in the present invention.
Figure 5B:
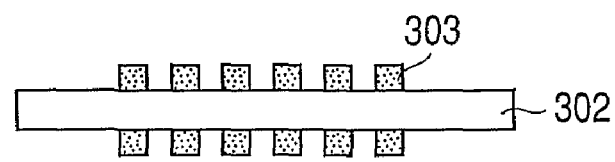
Figure 5C:
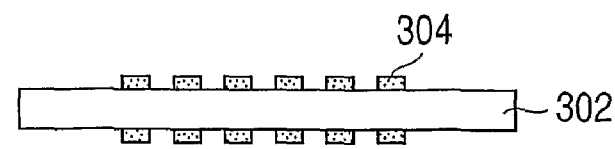

In the next place, a metallic structure will be described while focusing on a production method. Some cases out of metallic structures according to the present invention can be referred to as a metallic pattern. In order to easily produce the metallic structure and can enhance the yield, the metallic structure can be the metallic pattern formed on a substrate, as is illustrated in FIGS. 5B and 5C. FIG. 5A illustrates an example of a detecting element having a fine metallic particle 301 formed on two principal surfaces of a tabular substrate 302; and FIGS. 5B and 5C illustrate an example of the detecting element having the metallic structure 303 formed of the metallic pattern formed on the two principal surfaces of the tabular substrate 302. The metallic structure with the use of the metallic pattern is better than that with the use of the fine metallic particle according to the following reason. It is considered that partial aggregation incidentally occurs when the fine metallic particle is employed for the metallic structure, as is illustrated in FIG. 5A. Then, the aggregated particles show different characteristics from those of the single fine metallic particle, consequently cause variations in a detected spectrum, and may decrease the sensitivity of a sensor. On the other hand, when the element employs the metallic pattern, the element prevents the above described aggregation from forming thereon, can adjust a space between fine metallic structures, and can easily control the characteristics of a spectrum to be detected. Specifically, the element having the metallic pattern shows an improved accuracy of the spectrum.

An example illustrated in FIG. 5C is similar to the example illustrated in FIG. 5B, but is different from the example illustrated in FIG. 5B in a point of a shape of a metallic structure 304. The example illustrated in FIG. 5C has a flat shape of the metallic structure. A metallic pattern can be the flat shape. This is because the smaller is an aspect ratio of the metallic structure, the larger is a change of a plasmon resonance condition in response to a change of a refractive index, which occurs in the surroundings. In the above description, "aspect ratio of metallic structure" is defined as a quotient of the maximum length in a direction perpendicular to the surface of a substrate, on which the metallic structure is formed, divided by the maximum length in the direction parallel to the surface on which the metallic structure is formed, in a cross section formed by cutting the metallic structure in a plane perpendicular to the surface of a substrate, on which the metallic structure is formed. In addition, the flat shape means a planar shape having an aspect ratio of ½ or less, in the present invention. The aspect ratio can be ¼ or less.

Another example of a shape of a metallic pattern includes the shapes as are illustrated in FIGS. 6B to 6J. The above FIGS. 6A to 6J are sectional views in which a metallic structure is cut in a plane parallel to the surface of a substrate, on which the metallic structure is formed.

When producing a metallic structure on a plane with various film-forming methods, it is difficult to measure the size of the metallic structure with an instrument for measuring a particle diameter. In such a case, the size of the metallic structure can be as described below. At first, thickness (average thickness in a direction perpendicular to a plane having the metallic structure formed thereon) can be 10 nm or larger but 100 nm or smaller. In addition, the size (the maximum value of the space between arbitrary two points in a metallic structure on a plane parallel to the plane having the metallic structure formed thereon) can be 10 nm or larger but 1,450 nm or smaller, and further can be 50 nm or larger but 450 nm or smaller.

A space between metallic structures (the shortest length between adjacent metallic structures) can be 50 nm or longer but 2 µm or shorter, and further can be 150 nm or longer but 1 µm or shorter. As described in the description of the space between planes having the metallic structure formed thereon, when the space between metallic structures is too short, plasmon existing in metallic structures interact with each other and affect a distribution/intensity of a spatial electric field. As a result of this, the sensitivity of a sensor may decrease. On the other hand, when the space is too long, signal intensity becomes weak because the density of the metallic structure is low, which requires a specific optical system for enhancing sensitivity.

In addition, when a plane does not have a satisfactory size on a substrate (the substrate does not have the plane with the satisfactory size), it is difficult to form a metallic pattern thereon. Accordingly, the plane needs to have a satisfactory size for making the metallic structure exist thereon, from the viewpoint of facilitating the production of a detecting element.

In the next place, a capturing body and a target substance will be described.

(Capturing Body and Target Substance)

A capturing body is arranged on the surface of a metallic structure or in the vicinity of the metallic structure.

Any material can be used as a capturing body without particular limitation, as long as it can selectively and specifically capture a target substance. In the above description, "selectively capturing a target substance" means that the capturing body has a particularly strong force of capturing the target substance although capturing a plurality of substances, and "specifically capturing the target substance" means that the capturing body captures only the target substance.

A capturing body according to the present invention includes the one which recognizes a shape and a size of a target substance with the use of a three-dimensional structure of a macromolecular compound; and the one which recognizes the target substance with the use of a hydrogen bond, a coordinate bond, an electrostatic interaction and a hydrophobic area. Alternatively, the capturing body may be the one which recognizes the target substance by using some of the structures, the bonds and the action in combination. As described above, "capturing" in the present invention and the present specification is a concept which widely includes a general function of recognizing the substance by using various interactions. In addition, the target substance to be captured by the capturing body is not only a comparatively small substance such as a molecule and an ion, but also may be an aggregate of molecules or a cell.

A specific capturing reaction between a target substance and a capturing body for the target substance may be any type of an interaction, as long as an amount of a physical/chemical change before and after the capturing reaction can be detected by a detecting element according to the present invention. The interaction can include an antigen-antibody reaction, an antigen-aptamer (RNA fragment with specific structure) interaction, a ligand-receptor interaction, DNA hybridization, a DNA-protein (such as transcription factor) interaction, and a lectin-sugar chain interaction. Accordingly, a combination of the target substance and the capturing body for the target substance can be determined to be such a combination as to cause the above described interactions or the above described reactions (such as antigen-antibody reaction).

A target substance may be any substance as long as the substance can be selectively or specifically captured by a capturing body through an arbitrary interaction such as the above described interactions, and the phenomenon can be detected by a detecting element according to the present invention. Such a substance can be an object to be detected.

A representative example of a target substance and a capturing body includes a substance related to a living body. The substance related to a living body includes a molecule related to a living body selected from the group consisting of nucleic acid, protein, sugar chain, fat and a complex of them. More specifically, an example of the capturing body or the target substance can include any one selected from the group consisting of DNA, RNA, aptamer, a gene, a chromosome, a cell membrane, a virus, an antigen, an antibody, lectin, hapten, hormone, a receptor, an enzyme and a peptide. In addition, a bacterium or a cell in itself, which produces the above described "biological substance", is also considered to be a "biological substance" and can be the target substance and the capturing body.

In the next place, a detecting device with the use of the above described detecting element will be described.

Figure 7A:
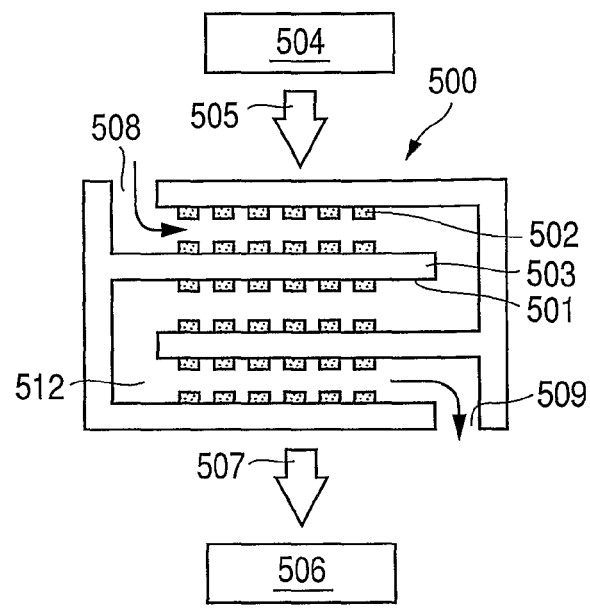
FIGS. 7A and 7B are conceptual diagrams illustrating one example of a configuration of a detecting device according to the present invention.
Figure 7B:
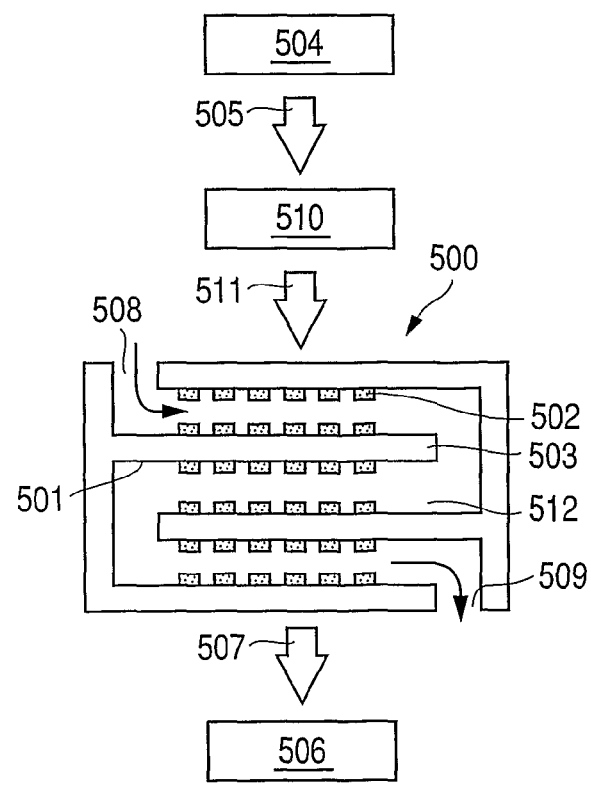

FIGS. 7A and 7B are conceptual diagrams illustrating an example of a configuration of a detecting device in the present invention. The detecting device according to the present example is a device for optically detecting characteristics of an analyte, and has: the above described detecting element 500; a light source 504 for irradiating the above described detecting element 500 with a detecting light 505; a light receiving element 506 for receiving the light (transmitted light) 507 having passed through the above described detecting element 500; and an arithmetic unit (not illustrated) for determining the characteristics of the analyte from a signal obtained by the above described received light.

A detecting element 500 is similar to the element illustrated in FIG. 3, and is produced by combining a plurality of substrates 503 having a plane 501 having a metallic structure 502 arranged thereon. In the figure, 508 is an inlet for an analyte, 509 is an outlet for the analyte, and a gap existing in between the inlet 508 and the outlet 509 is one part of a duct for the analyte (analyte-holding region 512). In addition, the metallic structure 502 has a capturing body (not illustrated) for capturing a target substance in the analyte immobilized on the surface.

A detecting device according to the present invention employing the above described configuration enables an operation of detecting a target substance in an analyte to be continuously performed. Specifically, the detecting device can arrange a unit for performing a series of steps up to detecting quantitative information such as concentration related to the target substance in the analyte, in one device, by immobilizing a capturing body for capturing the target substance, on the detecting element 500, charging the analyte containing the target substance into the detecting element 500, and irradiating the detecting element 500 with a detecting light 505.

In the next place, a light source 504, a light receiving element 506 and an arithmetic unit (not illustrated) will be sequentially described, which compose a detecting device 500 illustrated in FIGS. 7A and 7B.

(Light Source)

A detecting light to be used in the present invention may be any type, as long as the light has a range of wavelengths that cause plasmon resonance with a metallic structure. Accordingly, various types of light such as a laser and LED can be used for a light source. The light source can include a halogen lamp, a tungsten lamp and a xenon lamp, all of which are a white light source having a wide range of wavelengths. In addition, a detecting device according to the present invention may have various optical systems in between the light source and a detecting element. An example of such an optical system includes: a lens optical system for adjusting an irradiating region of a detecting light (which is also an output light 505 of the light source in the example illustrated in FIG. 7A) to a detecting element; an optical system (a collimator) for collimation; and a spectral optical system such as a polarizing plate for polarizing the detecting light and a monochromator. The detecting device illustrated in FIG. 7B is an example which has the spectral optical system 510 formed of the monochromator installed in between the light source 504 and the detecting element 501. Thereby, the optical system 510 makes the light 505 emitted from the light source to be incident on the detecting element as monochromatic light 511. Except the point, the detecting device has the same configuration as in the case of the device illustrated in FIG. 7A.

The various optical systems can be placed not only in between a light source 504 and a detecting element 500, but also at an arbitrary position in an optical path for a detecting light.

(Light Receiving Element)

A light receiving element 506 can be any type as long as it can detect characteristics of a light 507 having passed through a detecting element 500, but needs to be selected so as to suit the change of the characteristics to be used for detection. When detecting the change of the intensity of the transmitted light, a photodiode or a photomultiplier (PMT) can be used as the light receiving element. When detecting the change of a spectrum, it is possible to use a detector (so-called spectrometer) with the use of a spectral optical system. When using the spectral optical system, it is acceptable to measure the spectrum by passing the light having passed through a detecting element in a spectroscope such as a monochromator and a polychromator. However, it is also acceptable to measure a spectrum by dispersing light with the use of a spectral optical system 510 such as a monochromator, before the light irradiates the detecting element, changing a wavelength of the dispersed light and measuring the intensity of the transmitted light, as in the example illustrated in FIG. 7B described above.

(Arithmetic Unit)

An arithmetic unit in a detecting device according to the present example is a unit for calculating the change of characteristic's of a transmitted light, which has been caused by that an analyte has contacted with a metallic structure 502 of a detecting element 500, based on a signal obtained from the above described light receiving element 506. More specifically, the arithmetic unit calculates whether a target substance in the analyte has been captured by a capturing body or not, when the analyte has contacted with the metallic structure 502 of the detecting element 500, and calculates an amount of the target substance, when the analyte has been captured. The arithmetic unit is a unit for detecting the change of the intensity of the transmitted light 507 when processing the intensity as a signal, or detecting the change of a spectrum of the transmitted light 507 when processing the spectrum as the signal, and accordingly can be provided with a mechanism for processing the change of the characteristics as the signal. The arithmetic unit can be further provided with a mechanism which can quantitatively evaluate the characteristics by processing the signal. Such a mechanism includes a mechanism which can calculate an amount of the target substance by, for instance, comparing the change of the characteristics of the transmitted light with a previously acquired data that shows a correlation between the amount of the target substance and the change of the characteristics of the transmitted light.

A detecting device can have a configuration of using a transmitted light for an output light as is shown in FIGS. 7A and 7B, because a detecting element according to the present invention absorbs a detecting light most frequently in the vicinity of a metallic structure. However, the detecting device can employ a configuration of making the detecting light pass through a plane having the metallic structure arranged thereon two or more times and reflect, and detecting the reflected light as the output light. The detecting device can employ a configuration of, for instance, forming a substrate which has the plane having the metallic structure arranged thereon and is farthest from a light source, with a material having a high reflectivity. In such a case, a light receiving element is not placed in an opposite side to the light source with respect to the detecting element, as in the case of FIGS. 7A and 7B, but is placed in the same side as the light source with respect to the detecting element. When making the detecting light perpendicularly or generally perpendicularly incident on the detecting element, pass through the plane having the metallic structure arranged thereon two or more times, and using the reflected light as the output light, the output light can be separated from the detecting light by a light splitter.

A detecting device according to the present invention can have a device (such as display unit) for outputting a result. The device for outputting the result may exist separately from an arithmetic unit, or may be integrated into the arithmetic unit.

In the next place, a detecting method according to the present invention will be described.

A detecting method according to the present invention has the steps of: introducing an analyte into the above described detecting element; making a detecting light irradiate the detecting element so that the light intersects a plane having a plurality of mutually-separated metallic structures arranged on the detecting element; making a light receiving element receive the light emitted from the detecting element; and determining characteristics of an analyte based on the signal output from the above described light receiving element.

The detecting method according to the present invention can be realized by using the detecting device, for instance, in the example illustrated in FIGS. 7A and 7B described above.

EMBODIMENTS

Embodiment 1

Embodiment 1 will be now described with reference to FIGS. 7A, 7B and 8.

<Preparation Of Detecting Element>

Figure 6B:
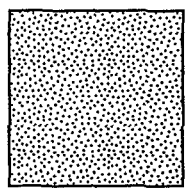
Figure 6C:
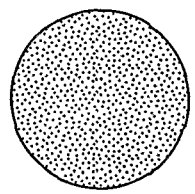
Figure 6D:
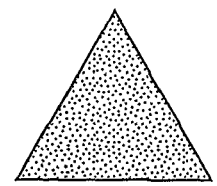
Figure 6E:
Figure 6F:
Figure 6G:
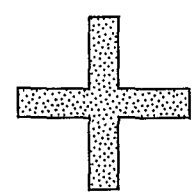
Figure 6H:
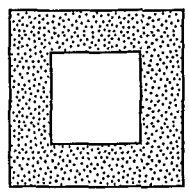
Figure 6I:
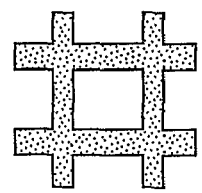
Figure 6J:
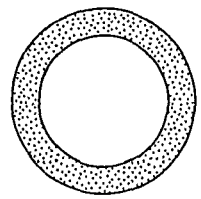

A detecting element is prepared by the steps of: previously forming an adhesive layer of Ti on a quartz substrate with a thickness of 0.725 mm; then forming a gold thin film with a thickness of 20 nm on the surface of the adhesive layer with a sputtering technique; applying a negative resist onto the gold thin film; exposing a square part of 200 nm by 200 nm in the negative resist to light by using an electron-beam lithographic apparatus to form a square resist pattern; etching a part of the gold thin film and the adhesive layer, which is not covered with the resist that functions as a mask, by using an ICP etcher; and after the etching step, removing the resist that has been used as the mask, by using an asher. Through the above steps, a gold pattern as illustrated in FIG. 6B is formed on a substrate, which consists of isolated gold thin films from each other having a square shape of 200 nm per side, and thus, the substrate is prepared which has a plurality of metallic structures arranged on one principal surface so that they can be separated from each other. In the above example, an electron-beam lithographic apparatus has been used, but it is acceptable to form the pattern by using a focused ion-beam processing apparatus, an X-rays-exposing apparatus, an ultraviolet-light-exposing apparatus or an excimer-laser-exposing apparatus. In addition, in the above example, a method by using an etching technique was described, but the detecting element may be prepared by using a lift-off technology as well.

Figure 8:
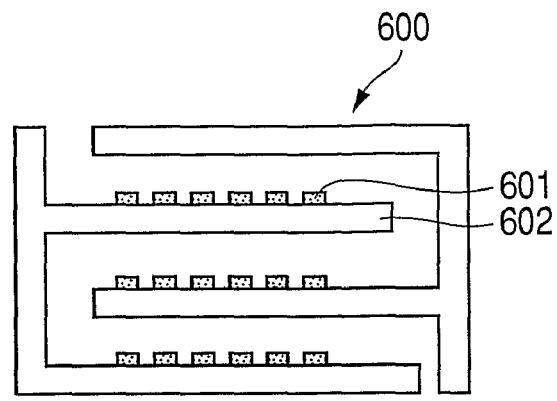
FIG. 8 is a schematic block diagram illustrating a configuration of the detecting element according to Embodiment 1 in the present invention.

A detecting element 600 as illustrated in FIG. 8 is prepared by setting thus obtained three substrates 602 in parallel, each of which has a plurality of metallic structures 601 made from gold arranged on its one principal surface so as to be separated from each other.

<Detecting Device>

Figure 9:
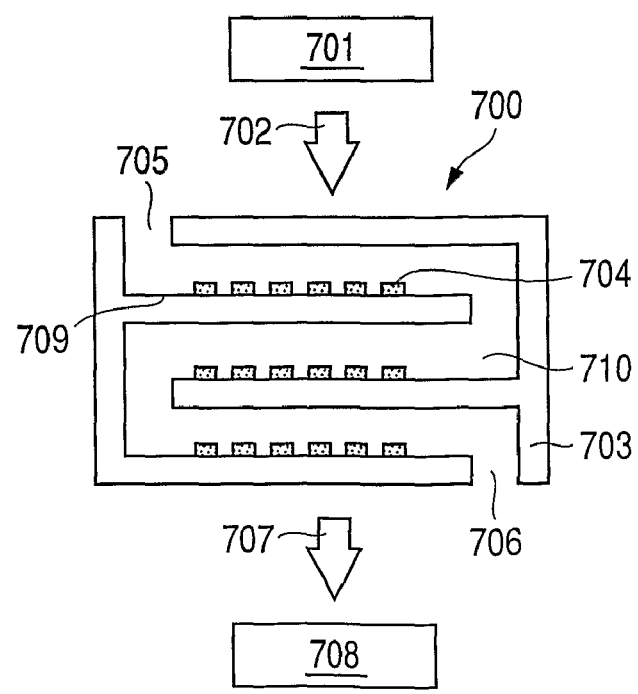
FIG. 9 is a schematic block diagram illustrating a configuration of the detecting device according to Embodiment 1 in the present invention.

FIG. 9 is a block diagram of a detecting device according to the present embodiment.

The detecting device consists of a halogen lamp 701 which is a light source, a detecting element 700, and a spectrometer 708 which is a light receiving element. The detecting element 700 shown in the FIG. 9 has the same structure as the detecting element 600 shown in FIG. 8. A plane 709 belongs to a substrate 703 and has a metallic structure arranged thereon, and an analyte-holding region 710 has the plane 709 having the metallic structure arranged thereon, the metallic structure 704 and the substrate 703. The detecting element has one part of a duct formed in itself. The analyte-holding region 710 is the one part of the duct. In the detecting element, an inlet 705 and an outlet 706 are installed for introducing an analyte and cleaning the inner part. In addition, 704 is the metallic structure made from gold, 702 is a detecting light emitted toward the detecting element and 707 is the light (transmitted light) having passed through the detecting element.

<Detecting Method>

A detecting method according to the present embodiment will be now described in detail with reference to FIG. 10.

Figure 10:
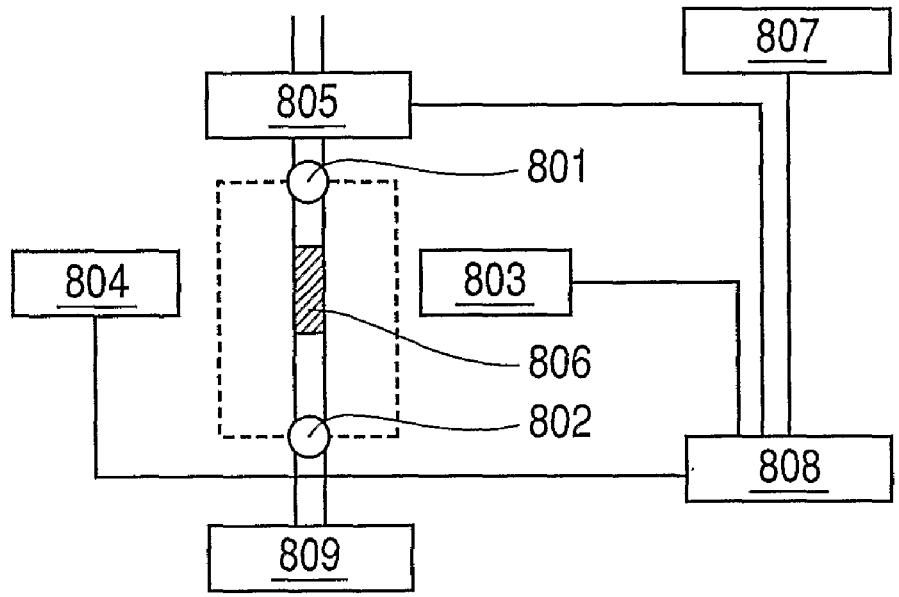
FIG. 10 is a block diagram according to Embodiment 1 in the present invention.

An inlet 801 and an outlet 802 are connected to another part of a duct (a part connected with a liquid supply pump 805 and a part connected with a waste water reservoir 809) in a detecting element, as is illustrated in FIG. 10. Then, the detecting element is aligned so that the reaction zone (zone having metallic structure arranged thereon) 806 can be positioned on an optical axis which connects a sensor 803 provided with a spectrometer (light receiving element) and a light source unit 804 that uses a halogen lamp as a light source. In this state before the metallic structure is subjected to a reaction, a spectrum is previously detected with the use of a spectrometer. Subsequently, the surface of the metallic structure made from gold is modified by driving the liquid supply pump 805 to supply an ethanol solution of 11-mercaptoundecanoic acid having a thiol group with a high affinity for gold into the element (into an analyte-holding region). Then, a succinimide group is fixed on the surface of the metallic structure by supplying an aqueous solution of n-hydroxysulfosuccinimide (made by Dojindo Laboratories Corporation) and an aqueous solution of 1-Ethyl-3-[3-dimethylamino]propyl]carbodiimide hydrochloride (made by Dojindo Laboratories Corporation) into the element (into the analyte-holding region). Subsequently, the antihuman CRP antibody that specifically captures human CRP which is a target substance is immobilized on the detecting element as an antibody to be immobilized, by introducing a tris-hydrochloric acid buffer solution (pH 8.0) containing the antihuman CRP antibody into the element. Next, a predetermined amount of the human CRP is supplied to the reaction zone 806 of the detecting element. Then, the antihuman CRP antibody captures the human CRP which is the target substance, through an antigen-antibody reaction between the human CRP and the antihuman CRP antibody. After the reaction, a spectrum is measured with the spectrometer. A central operator 808 which is an arithmetic unit compares the spectrum obtained in this step, with the spectrum before the metallic structure has been subjected to the reaction. The difference shows a change of a localized surface plasmon resonance state of the detecting element, which originates from the result that the capturing body on the detecting element has captured the target substance in the vicinity of the detecting element. The change of the localized surface plasmon resonance state is displayed on a display unit 807 which is a display device.

In the present embodiment, the central operator 808 in the arithmetic unit determines a concentration of a target substance from a degree of the change of a spectrum, and displays the result on the display unit 807. A relationship between the change of the spectrum and the concentration of the target substance is previously acquired with the use of known normal analytes having a plurality of concentrations. Furthermore, a function showing the relation between the change of the spectrum and the concentration is previously determined by making a calibration curve on the basis of the relationship. The concentration of the target substance of which the concentration is unknown can be determined by using the function and the obtained change of the spectrum, when actually measuring the concentration. In the above description, the change of the spectrum was simply described, but the change of the spectrum may be the change of a spectral peak (change of a wavelength showing the maximum absorbance), or may be the change of a peak shape such as a full width at the half maximum of the peak, in the spectrum. Furthermore, the change of the intensity of light at one or more wavelength points may be used.

Embodiment 2

Embodiment 2 will be now described with reference to FIGS. 10 and 11.
<Preparation of Detecting Element>

The whole surface of a glass substrate 901 (made by Matsunami Glass Ind., Ltd.) is previously modified with an amino group. Then, the glass substrate 901 is immersed in a solution of a fine gold particle 902 with an average particle diameter of 40 nm (made in Tanaka Kikinzoku Kogyo K. K.) for 24 hours, is washed with pure water, and is dried with nitrogen gas.

Subsequently, a capturing body for capturing a target substance is immobilized on the surface of a fine gold particle by the following steps of: firstly, adding an ethanol solution of 11-mercaptoundecanoic acid having a thiol group having a high affinity for gold to modify the surface of the fine gold particle; then, making the modified surface contact with an aqueous solution of n-hydroxysulfosuccinimide (made by Dojindo Laboratories Corporation) and the aqueous solution of 1-ethyl-3-[3-dimethylamino]propyl]carbodiimide hydrochloride (made by Dojindo Laboratories Corporation) to make the succinimide group exposed at the surface of the fine gold particle; subsequently, adding a tris-hydrochloric acid buffer solution (pH 8.0) containing an antihuman CRP antibody which specifically captures human CRP that is the target substance, dropwise onto the surface of the fine gold particle, as an antibody to be immobilized; thus reacting the above described succinimide group arranged on the surface of the fine gold particle with the amino group of the antihuman CRP antibody to immobilize the antihuman CRP antibody 903 on the surface of the fine gold particle 902; and desorbing an unreacted succinimide group remaining on the surface of the fine gold particle by adding hydroxylamine hydrochloride. Thus, a substrate is prepared which has fine gold particles having the antihuman CRP antibody 903 of the capturing body immobilized on two principal surfaces that face to each other, as is illustrated in FIG. 11. The substrate is used as one part of a detecting element.

Figure 11:
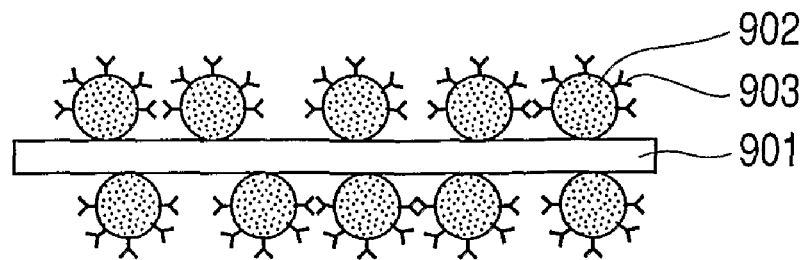
FIG. 11 is a schematic block diagram illustrating a configuration of the detecting element according to Embodiment 2 in the present invention.
Figure 12:
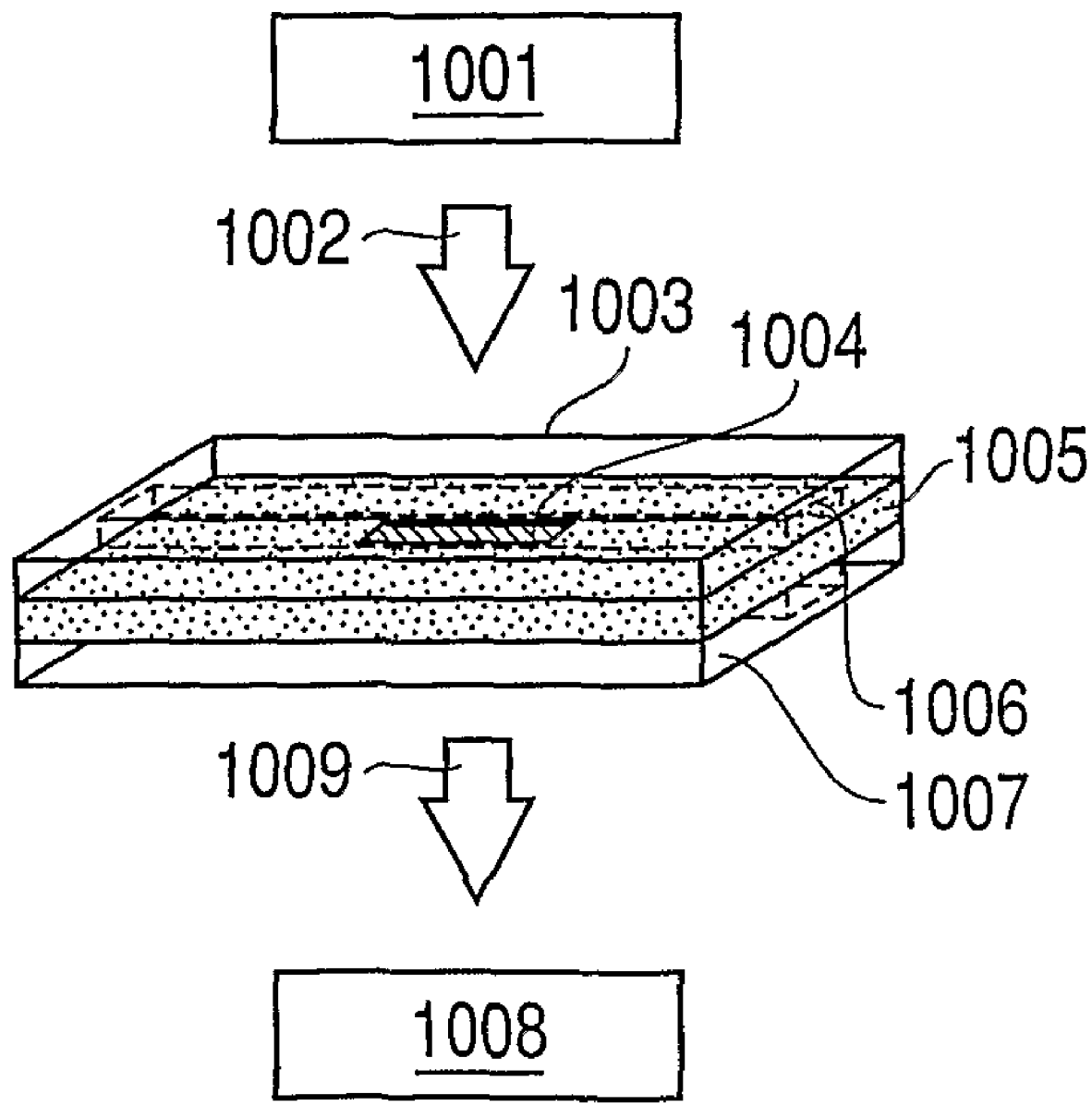
FIG. 12 is a schematic block diagram illustrating a configuration of the detecting device according to Embodiment 2 in the present invention.

As is illustrated in FIG. 12, a detecting element 1003 is prepared by arranging a polydimethylsiloxane (hereafter referred to as PDMS) chip 1007 provided with one groove, on each of both surfaces of such a substrate 1005 (that is the same as the substrate shown in FIG. 11, which has fine gold particles having an antihuman CRP antibody 903 immobilized on the two principal surfaces that face to each other). An analyte-holding region 1006 (one part of a duct) can be formed by arranging the groove in a substrate 1005 side. Then, one part of the analyte-holding region 1006 becomes a reaction zone 1004.
<Configuration of Detecting Device>

Subsequently, a configuration of a detecting device to be used in the present embodiment will be described with reference to FIG. 12.

The detecting device according to the present embodiment has: a green semiconductor laser 1001 with a luminescence center wavelength of 532 nm, which is a light source; a detecting element 1003; and a photodiode 1008 as a light receiving element for a transmitted light. These components are arranged so that a detecting light 1002 can irradiate a reaction zone 1004, and a light (transmitted light) 1009 having transmitted through the detecting element can be incident on the photodiode 1008.
<Detecting Method>

The detecting device according to the present embodiment also can detect a target substance through the same detecting process as in the case of Embodiment 1. However, the detecting device according to the present embodiment employs a semiconductor laser for a light source unit and a photodiode for a light receiving element.

In addition, the detecting method in the present embodiment skips a step of immobilizing an antihuman CRP antibody in a detecting step, because the antihuman CRP antibody of a capturing body for a target substance is already immobilized on a fine gold particle.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-133847, filed May 12, 2006, which is hereby incorporated by reference herein in its entirety.

The invention claimed is:

1. A detecting element for detecting a property of an analyte by using a detecting light, comprising:
   a plurality of metallic structures separated from each other;
   a plurality of substrates which has a plurality of planes on which the metallic structures exist; and
   an analyte-holding region constituting a duct for the analyte,
   wherein at least one part of the analyte-holding region is comprised of a part of at least one of the planes, and one of the planes has a normal line intersecting with all the other planes,
   wherein the planes are arranged such that the detecting light intersects the planes, and
   wherein the normal line intersecting with the other planes is on an angle of 20 degrees or less with the detecting light.

2. The detecting element according to claim 1, wherein the plane having the normal line is one arbitrarily selected from the planes.

3. The detecting element according to claim 1, wherein at least one of the metallic structures has a surface by which a capturing body for capturing a target substance contained in the analyte is held.

4. The detecting element according to claim 1, wherein the metallic structures are patterned and have their respective flat shapes.

5. The detecting element according to claim 1, wherein the duct for the analyte is formed by combining the substrates with one another, and wherein the duct for the analyte includes a turn.

6. A detecting device for detecting a property of an analyte, comprising
   a detecting element;
   a light source for irradiating the detecting element with a detecting light;
   a light receiving element for receiving an output light emitted from the detecting element; and
   an arithmetic unit for processing a signal obtained by the light receiving element to determine the property of the analyte,
   wherein the detecting element comprises a plurality of metallic structures separated from each other, a plurality of substrates which has a plurality of planes on which the metallic structures exist, and an analyte-holding region constituting a duct for the analyte,
   wherein at least one part of the analyte-holding region is comprised of a part of at least one of the planes, and one of the planes has a normal line intersecting with all the other planes,
   wherein the planes are arranged such that the detecting light intersects the planes, and
   wherein the normal line intersecting with the other planes is on an angle of 20 degrees or less with the detecting light.

7. The detecting device according to claim 6, wherein the plane having the normal line is one arbitrarily selected from the planes.

8. The detecting device according to claim 6, wherein at least one of the metallic structures has a surface by which a capturing body for capturing a target substance contained in the analyte is held.

9. The detecting device according to claim 6, wherein the duct for the analyte is formed by combining the substrates with one another, and wherein the duct for the analyte includes a turn.

10. A method for detecting a property of an analyte using a detecting element which is comprised of a plurality of metallic structures separated from each other, a plurality of substrates which has a plurality of planes on which the metallic structures exist, and an analyte-holding region constituting a duct for the analyte, wherein at least one part of the analyte-holding region is comprised of a part of at least one of the planes, which comprises the steps of:
   introducing an analyte into the analyte-holding region;
   irradiating the detecting element with a detecting light so that the detecting light intersects the planes;
   receiving the output light emitted from the detecting element with a light receiving element;
   determining a property of the analyte by a signal output from the light receiving element; and
   outputting the determined property to a user,
   wherein each normal line of the planes is on an angle of 20 degrees or less with the detecting light.

11. The detecting method according to claim 10, wherein the duct for the analyte is formed by combining the substrates with one another, and wherein the duct for the analyte includes a turn.

* * * * *